US008500760B2

(12) United States Patent
McLawhorn

(10) Patent No.: US 8,500,760 B2
(45) Date of Patent: Aug. 6, 2013

(54) RETRACTABLE TACKING DEVICE

(75) Inventor: Tyler E. McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 608 days.

(21) Appl. No.: 12/632,300

(22) Filed: Dec. 7, 2009

(65) Prior Publication Data

US 2010/0140320 A1    Jun. 10, 2010

Related U.S. Application Data

(60) Provisional application No. 61/121,067, filed on Dec. 9, 2008.

(51) Int. Cl.
*A61B 17/08* (2006.01)
*A61B 17/10* (2006.01)

(52) U.S. Cl.
USPC .......................................... 606/151; 606/142

(58) Field of Classification Search
USPC ............. 606/74, 75, 127, 139, 142, 143, 151, 606/157, 200, 213, 215, 216, 219, 220, 232, 606/326; 623/23.72
See application file for complete search history.

(56) References Cited

U.S. PATENT DOCUMENTS

| 2,199,025 A | 4/1940 | Conn |
| 2,671,444 A | 3/1954 | Pease, Jr. |
| 3,209,422 A | 10/1965 | Dritz |
| 3,399,432 A | 9/1968 | Merser |
| 3,470,834 A | 10/1969 | Bone |
| 3,556,079 A | 1/1971 | Omizo |
| 3,814,104 A | 6/1974 | Irnich et al. |

(Continued)

FOREIGN PATENT DOCUMENTS

| EP | 0310582 A1 | 4/1989 |
| EP | 0774237 A2 | 5/1997 |

(Continued)

OTHER PUBLICATIONS

Communication Pursuant to Rules 161(1) and 162EPC for European Patent Application Serial No. 09791618.3, dated Mar. 28, 2011, 2 pages.

(Continued)

*Primary Examiner* — Ryan Severson
*Assistant Examiner* — Ashley Fishback
(74) *Attorney, Agent, or Firm* — Brinks Hofer Gilson & Lione

(57) ABSTRACT

The present embodiments provide a tacking device for engaging tissue, which may be useful for coupling a graft to tissue or facilitating closure of a bodily opening. In one embodiment, the tacking device comprises a main body having proximal and distal ends, and further comprises at least one proximal deployable member and at least one distal deployable member, each having contracted and expanded states. The proximal deployable members extend proximally from the proximal end of the main body, while the distal deployable members extend distally from the distal end of the main body. In one embodiment, a hook member extends from at least one of the proximal deployable members. In use, the hook member may be engaged, for example, using a loop member coupled to a stylet, thereby facilitating controlled release of the tacking device and allowing repositioning of the tacking device after at least partial deployment of the distal deployable members.

5 Claims, 8 Drawing Sheets

U.S. PATENT DOCUMENTS

| | | | |
|---|---|---|---|
| 3,856,016 A | 12/1974 | Davis | |
| 3,954,108 A | 5/1976 | Davis | |
| 3,958,576 A | 5/1976 | Komiya | |
| 4,006,747 A | 2/1977 | Kronenthal et al. | |
| 4,204,541 A | 5/1980 | Kapitanov | |
| 4,217,902 A | 8/1980 | March | |
| 4,235,238 A | 11/1980 | Ogiu et al. | |
| 4,485,816 A | 12/1984 | Krumme | |
| 4,621,639 A | 11/1986 | Transue et al. | |
| 4,749,114 A | 6/1988 | Green | |
| 4,773,420 A | 9/1988 | Green | |
| 4,791,707 A | 12/1988 | Tucker | |
| 4,796,627 A | 1/1989 | Tucker | |
| 4,821,939 A | 4/1989 | Green | |
| 4,832,027 A | 5/1989 | Utz | |
| 4,990,156 A | 2/1991 | Lefebvre | |
| 5,015,249 A | 5/1991 | Nakao et al. | |
| 5,049,153 A | 9/1991 | Nakao et al. | |
| 5,059,205 A | 10/1991 | El-Nounou et al. | |
| 5,084,057 A | 1/1992 | Green et al. | |
| 5,099,827 A | 3/1992 | Melzer et al. | |
| 5,100,420 A | 3/1992 | Green et al. | |
| 5,123,914 A | 6/1992 | Cope | |
| 5,156,609 A | 10/1992 | Nakao et al. | |
| 5,192,303 A | 3/1993 | Gatturna et al. | |
| 5,203,787 A | 4/1993 | Noblitt et al. | |
| 5,242,456 A | 9/1993 | Nash et al. | |
| 5,324,307 A | 6/1994 | Jarrett et al. | |
| 5,333,624 A | 8/1994 | Tovey | |
| 5,334,217 A | 8/1994 | Das | |
| 5,350,385 A | 9/1994 | Christy | |
| 5,366,480 A | 11/1994 | Corriveau et al. | |
| 5,368,600 A | 11/1994 | Failla et al. | |
| 5,368,602 A | 11/1994 | de la Torre | |
| 5,411,522 A | 5/1995 | Trott | |
| 5,417,691 A | 5/1995 | Hayhurst | |
| 5,437,266 A | 8/1995 | McPherson | |
| 5,520,700 A | 5/1996 | Beyar et al. | |
| 5,527,343 A | 6/1996 | Bonutti | |
| 5,554,183 A | 9/1996 | Nazari | |
| 5,573,543 A | 11/1996 | Akopov et al. | |
| 5,582,615 A | 12/1996 | Foshee et al. | |
| 5,582,616 A | 12/1996 | Bolduc et al. | |
| 5,593,414 A | 1/1997 | Shipp et al. | |
| 5,662,683 A | 9/1997 | Kay | |
| 5,667,527 A | 9/1997 | Cook et al. | |
| 5,674,231 A | 10/1997 | Green et al. | |
| 5,690,656 A | 11/1997 | Cope et al. | |
| 5,695,525 A | 12/1997 | Mulhauser et al. | |
| 5,728,116 A | 3/1998 | Rosenman | |
| 5,741,278 A | 4/1998 | Stevens | |
| 5,779,720 A | 7/1998 | Walder-Utz et al. | |
| 5,810,848 A | 9/1998 | Hayhurst | |
| 5,865,791 A | 2/1999 | Whayne et al. | |
| 5,868,763 A | 2/1999 | Spence et al. | |
| 5,891,159 A | 4/1999 | Sherman et al. | |
| 5,968,078 A | 10/1999 | Grotz | |
| 5,972,002 A | 10/1999 | Bark et al. | |
| 5,972,022 A | 10/1999 | Huxel | |
| 5,976,159 A | 11/1999 | Bolduc et al. | |
| 5,984,917 A | 11/1999 | Fleischman et al. | |
| 5,984,949 A | 11/1999 | Levin | |
| 6,110,183 A | 8/2000 | Cope | |
| 6,113,612 A | 9/2000 | Swanson et al. | |
| RE36,974 E | 11/2000 | Bonutti | |
| 6,149,658 A | 11/2000 | Gardiner et al. | |
| 6,152,935 A | 11/2000 | Kammerer et al. | |
| 6,152,937 A | 11/2000 | Peterson et al. | |
| 6,156,044 A | 12/2000 | Kammerer et al. | |
| 6,159,223 A | 12/2000 | Danks et al. | |
| 6,171,321 B1 | 1/2001 | Gifford, III et al. | |
| 6,183,486 B1 | 2/2001 | Snow et al. | |
| 6,193,732 B1 | 2/2001 | Frantzen et al. | |
| 6,228,055 B1 | 5/2001 | Foerster et al. | |
| 6,241,747 B1 | 6/2001 | Ruff | |
| 6,251,122 B1 * | 6/2001 | Tsukernik | 606/200 |
| 6,290,674 B1 | 9/2001 | Roue et al. | |
| 6,306,150 B1 | 10/2001 | Levinson | |
| 6,328,727 B1 | 12/2001 | Frazier et al. | |
| 6,371,963 B1 | 4/2002 | Nishtala et al. | |
| 6,402,765 B1 | 6/2002 | Monassevitch et al. | |
| 6,419,669 B1 | 7/2002 | Frazier et al. | |
| 6,425,887 B1 | 7/2002 | McGuckin et al. | |
| 6,425,900 B1 | 7/2002 | Knodel et al. | |
| 6,428,548 B1 | 8/2002 | Durgin et al. | |
| 6,446,854 B1 | 9/2002 | Remiszewski et al. | |
| 6,447,530 B1 | 9/2002 | Ostrovsky et al. | |
| 6,468,290 B1 | 10/2002 | Weldon et al. | |
| 6,482,178 B1 | 11/2002 | Andrews et al. | |
| 6,491,707 B2 | 12/2002 | Makower et al. | |
| 6,551,333 B2 | 4/2003 | Kuhns et al. | |
| 6,572,629 B2 | 6/2003 | Kalloo et al. | |
| 6,592,559 B1 | 7/2003 | Pakter et al. | |
| 6,623,510 B2 | 9/2003 | Carley et al. | |
| 6,641,557 B1 | 11/2003 | Frazier et al. | |
| 6,699,256 B1 | 3/2004 | Logan et al. | |
| 6,699,263 B2 | 3/2004 | Cope | |
| 6,712,804 B2 | 3/2004 | Roue et al. | |
| 6,719,777 B2 | 4/2004 | Ginn et al. | |
| 6,746,458 B1 | 6/2004 | Cloud | |
| 6,746,460 B2 | 6/2004 | Gannoe et al. | |
| 6,746,472 B2 | 6/2004 | Frazier et al. | |
| 6,776,783 B1 | 8/2004 | Frantzen et al. | |
| 6,849,078 B2 | 2/2005 | Durgin et al. | |
| 6,884,248 B2 | 4/2005 | Bolduc et al. | |
| 6,911,032 B2 | 6/2005 | Jugenheimer et al. | |
| 6,913,607 B2 | 7/2005 | Ainsworth et al. | |
| 6,966,916 B2 | 11/2005 | Kumar | |
| 6,994,713 B2 | 2/2006 | Berg et al. | |
| 7,001,398 B2 | 2/2006 | Carley et al. | |
| 7,018,388 B2 | 3/2006 | Yencho et al. | |
| 7,025,756 B2 | 4/2006 | Frazier et al. | |
| 7,056,325 B1 | 6/2006 | Makower et al. | |
| 7,060,084 B1 | 6/2006 | Loshakove et al. | |
| 7,087,073 B2 | 8/2006 | Bonutti | |
| 7,112,214 B2 | 9/2006 | Peterson et al. | |
| 7,115,110 B2 | 10/2006 | Frazier et al. | |
| 7,211,101 B2 | 5/2007 | Carley et al. | |
| 7,326,221 B2 | 2/2008 | Sakamoto | |
| 7,326,231 B2 | 2/2008 | Phillips et al. | |
| 7,331,968 B2 | 2/2008 | Arp et al. | |
| 7,410,460 B2 | 8/2008 | Benderev | |
| 7,416,554 B2 | 8/2008 | Lam et al. | |
| 7,485,124 B2 | 2/2009 | Kuhns et al. | |
| 7,494,496 B2 | 2/2009 | Swain et al. | |
| 7,601,159 B2 | 10/2009 | Ewers et al. | |
| 7,608,091 B2 | 10/2009 | Goldbarb et al. | |
| 7,618,426 B2 | 11/2009 | Ewers et al. | |
| 7,621,925 B2 | 11/2009 | Saadat et al. | |
| 7,622,068 B2 | 11/2009 | Li et al. | |
| 7,641,836 B2 | 1/2010 | Li et al. | |
| 7,655,015 B2 | 2/2010 | Goldfarb et al. | |
| 7,666,197 B2 | 2/2010 | Orban, III | |
| 7,670,362 B2 | 3/2010 | Zergiebel | |
| 7,695,493 B2 | 4/2010 | Saadat et al. | |
| 7,704,264 B2 | 4/2010 | Ewers et al. | |
| 7,722,628 B2 | 5/2010 | Stokes et al. | |
| 7,727,247 B2 | 6/2010 | Kimura et al. | |
| 7,727,248 B2 | 6/2010 | Smith et al. | |
| 7,736,376 B2 | 6/2010 | Sato et al. | |
| 7,736,378 B2 | 6/2010 | Maahs et al. | |
| 7,736,379 B2 | 6/2010 | Ewers et al. | |
| 7,736,388 B2 | 6/2010 | Goldfarb et al. | |
| 7,744,613 B2 | 6/2010 | Ewers et al. | |
| 7,758,598 B2 | 7/2010 | Conlon et al. | |
| 7,758,612 B2 | 7/2010 | Shipp | |
| 7,799,040 B2 | 9/2010 | Stokes et al. | |
| 7,803,165 B2 | 9/2010 | Stokes et al. | |
| 7,803,166 B2 | 9/2010 | Stokes et al. | |
| 7,815,652 B2 | 10/2010 | Messerly et al. | |
| 7,815,653 B2 | 10/2010 | Stokes et al. | |
| 7,815,659 B2 | 10/2010 | Conlon et al. | |
| 7,815,662 B2 | 10/2010 | Spivey et al. | |
| 7,828,811 B2 | 11/2010 | Kortenbach et al. | |
| 8,092,485 B2 * | 1/2012 | Lapid | 606/200 |
| 2001/0002250 A1 | 5/2001 | Burbank et al. | |
| 2001/0037130 A1 | 11/2001 | Adams | |

| | | |
|---|---|---|
| 2001/0039435 A1 | 11/2001 | Roue et al. |
| 2003/0158578 A1 | 8/2003 | Pantages et al. |
| 2003/0195561 A1 | 10/2003 | Carley et al. |
| 2004/0009289 A1 | 1/2004 | Carley et al. |
| 2004/0039414 A1 | 2/2004 | Carley et al. |
| 2004/0044364 A1 | 3/2004 | Devries et al. |
| 2004/0073236 A1 | 4/2004 | Carley et al. |
| 2004/0087981 A1 | 5/2004 | Berube et al. |
| 2004/0087985 A1 | 5/2004 | Loshakove et al. |
| 2004/0092975 A1 | 5/2004 | Loshakove et al. |
| 2004/0097982 A1 | 5/2004 | Jugenheimer et al. |
| 2004/0133236 A1* | 7/2004 | Chanduszko ................ 606/213 |
| 2004/0167539 A1 | 8/2004 | Kuehn et al. |
| 2004/0186514 A1 | 9/2004 | Swain et al. |
| 2004/0220596 A1 | 11/2004 | Frazier et al. |
| 2005/0015141 A1 | 1/2005 | Quiachon et al. |
| 2005/0033313 A1 | 2/2005 | Chu et al. |
| 2005/0038370 A1 | 2/2005 | Kuth et al. |
| 2005/0113851 A1 | 5/2005 | Swain et al. |
| 2005/0119695 A1 | 6/2005 | Carley et al. |
| 2005/0143763 A1 | 6/2005 | Ortiz et al. |
| 2005/0165442 A1* | 7/2005 | Thinnes et al. ............... 606/200 |
| 2005/0171562 A1 | 8/2005 | Criscuolo et al. |
| 2005/0182445 A1 | 8/2005 | Zamierowski |
| 2005/0192596 A1 | 9/2005 | Jugenheimer et al. |
| 2005/0197594 A1 | 9/2005 | Burbank et al. |
| 2005/0234512 A1 | 10/2005 | Nakao |
| 2005/0251165 A1 | 11/2005 | Vaughan et al. |
| 2005/0277945 A1 | 12/2005 | Saadat et al. |
| 2005/0277981 A1 | 12/2005 | Maahs et al. |
| 2005/0283188 A1 | 12/2005 | Loshakove et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0015125 A1 | 1/2006 | Swain |
| 2006/0025788 A1 | 2/2006 | Loshakove et al. |
| 2006/0025819 A1 | 2/2006 | Nobis et al. |
| 2006/0106279 A1 | 5/2006 | Machold et al. |
| 2006/0106405 A1 | 5/2006 | Fann et al. |
| 2006/0116605 A1 | 6/2006 | Nakao |
| 2006/0135989 A1 | 6/2006 | Carley et al. |
| 2006/0155288 A1 | 7/2006 | Little et al. |
| 2006/0167484 A1 | 7/2006 | Carley et al. |
| 2006/0190016 A1 | 8/2006 | Onuki et al. |
| 2006/0190038 A1 | 8/2006 | Carley et al. |
| 2006/0206063 A1 | 9/2006 | Kagan et al. |
| 2006/0206138 A1* | 9/2006 | Eidenschink ................ 606/200 |
| 2006/0207606 A1 | 9/2006 | Roue et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241662 A1 | 10/2006 | Adams et al. |
| 2006/0241691 A1 | 10/2006 | Wilk |
| 2006/0253144 A1 | 11/2006 | Mikkaichi et al. |
| 2006/0271073 A1 | 11/2006 | Lam et al. |
| 2006/0271101 A1 | 11/2006 | Saadat et al. |
| 2007/0010835 A1 | 1/2007 | Breton et al. |
| 2007/0100375 A1 | 5/2007 | Mikkaichi et al. |
| 2007/0100376 A1 | 5/2007 | Mikkaichi et al. |
| 2007/0112362 A1 | 5/2007 | Mikkaichi et al. |
| 2007/0123840 A1 | 5/2007 | Cox |
| 2007/0129755 A1 | 6/2007 | Abbott et al. |
| 2007/0173868 A1 | 7/2007 | Bachinski et al. |
| 2007/0208360 A1 | 9/2007 | Demarais et al. |
| 2007/0219411 A1 | 9/2007 | Dejima et al. |
| 2007/0270752 A1 | 11/2007 | LaBombard |
| 2007/0270943 A1 | 11/2007 | Solem et al. |
| 2007/0276416 A1 | 11/2007 | Ginn et al. |
| 2007/0276424 A1 | 11/2007 | Mikkaichi et al. |
| 2008/0015633 A1 | 1/2008 | Abbott et al. |
| 2008/0086153 A1 | 4/2008 | Sakamoto et al. |
| 2008/0091059 A1 | 4/2008 | Machold |
| 2008/0097489 A1 | 4/2008 | Goldfarb et al. |
| 2008/0114378 A1 | 5/2008 | Matsushita |
| 2008/0114398 A1 | 5/2008 | Phillips et al. |
| 2008/0147116 A1 | 6/2008 | Smith et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0281354 A1 | 11/2008 | Cropper et al. |
| 2008/0294178 A1 | 11/2008 | Kortenbach et al. |
| 2008/0296344 A1 | 12/2008 | Cropper et al. |
| 2008/0300547 A1 | 12/2008 | Bakos |
| 2008/0300608 A1 | 12/2008 | Measamer |
| 2008/0300624 A1 | 12/2008 | Schwemberger et al. |
| 2008/0300627 A1 | 12/2008 | Measamer et al. |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0069822 A1 | 3/2009 | Takahashi et al. |
| 2009/0088780 A1 | 4/2009 | Shiono et al. |
| 2009/0088797 A1 | 4/2009 | Crombie et al. |
| 2009/0125038 A1 | 5/2009 | Ewers et al. |
| 2009/0125039 A1 | 5/2009 | Mikkaichi et al. |
| 2009/0204147 A1 | 8/2009 | Rahmani |
| 2009/0222029 A1 | 9/2009 | Gordin et al. |
| 2009/0287080 A1 | 11/2009 | Nishina et al. |
| 2009/0299385 A1 | 12/2009 | Stefanchik et al. |
| 2009/0299406 A1 | 12/2009 | Swain et al. |
| 2009/0306686 A1 | 12/2009 | Ohdaira |
| 2009/0318936 A1 | 12/2009 | Harris et al. |
| 2009/0326578 A1 | 12/2009 | Ewers et al. |
| 2010/0010457 A1 | 1/2010 | Ewers et al. |
| 2010/0010508 A1 | 1/2010 | Takahashi et al. |
| 2010/0010509 A1 | 1/2010 | Ishioka et al. |
| 2010/0010511 A1 | 1/2010 | Harris et al. |
| 2010/0010514 A1 | 1/2010 | Ishioka et al. |
| 2010/0010520 A1 | 1/2010 | Takahashi et al. |
| 2010/0042115 A1 | 2/2010 | Saadart et al. |
| 2010/0042144 A1 | 2/2010 | Bennett |
| 2010/0049244 A1 | 2/2010 | Cohen et al. |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0121351 A1 | 5/2010 | Whitfield et al. |
| 2010/0174312 A1 | 7/2010 | Maahs et al. |
| 2010/0198192 A1 | 8/2010 | Serina et al. |
| 2010/0211086 A1 | 8/2010 | Ewers et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0256658 A1 | 10/2010 | Criscuolo et al. |
| 2010/0264192 A1 | 10/2010 | Marczyk |
| 2010/0268253 A1 | 10/2010 | Ahlberg et al. |
| 2010/0268270 A1 | 10/2010 | Viola |
| 2011/0022065 A1 | 1/2011 | Shipp |

FOREIGN PATENT DOCUMENTS

| | | |
|---|---|---|
| EP | 1317904 A1 | 11/2003 |
| EP | 1961388 A2 | 8/2008 |
| WO | WO88/01486 | 3/1988 |
| WO | WO90/02522 | 3/1990 |
| WO | WO95/21575 | 8/1995 |
| WO | WO96/14020 | 5/1996 |
| WO | WO96/40356 | 12/1996 |
| WO | WO98/18389 | 5/1998 |
| WO | WO99/62408 | 12/1999 |

| | | |
|---|---|---|
| WO | WO00/07506 | 2/2000 |
| WO | WO00/16701 | 3/2000 |
| WO | WO00/21443 | 4/2000 |
| WO | WO00/56223 | 9/2000 |
| WO | WO00/56227 | 9/2000 |
| WO | WO01/19256 | 3/2001 |
| WO | WO01/35832 | 5/2001 |
| WO | WO01/58363 | 8/2001 |
| WO | WO2005/034729 | 4/2005 |
| WO | WO2007/004228 | 1/2007 |
| WO | WO2007/089843 | 8/2007 |
| WO | WO2007/142977 | 12/2007 |
| WO | WO2007/024615 | 3/2009 |

OTHER PUBLICATIONS

Response to Communication Pursuant to Rules 161(1) and 162EPC for European Patent Application Serial No. 09791618.3, dated May 6, 2011, 4 pages.
International Search Report for PCT/US2009/041415, dated Jul. 24, 2009, 4 pages.
International Preliminary Report on Patentability for PCT/US2009/041415, dated Nov. 4, 2010, 6 pages.
International Search Report for PCT/US2009/054176, dated Nov. 20, 2009, 16 pages.
International Preliminary Report on Patentability for PCT/US2009/054176, dated Mar. 3, 2011, 9 pages.
International Search Report for PCT/US2009/056512, dated Feb. 10, 2010, 5 pages.
Article 34 Demand and Amendment for PCT/US2009/056512, dated Jul. 6, 2010, 22 pages.
International Preliminary Report on Patentability for PCT/US2009/056512, dated Jan. 10, 2010, 31 pages.
International Search Report and Written Opinion for PCT/US2009/056604, dated May 4, 2010, 9 pages.
International Search Report for PCT/US2009/066983, dated Jan. 19, 2010, 4 pages.
International Search Report and Written Opinion for PCT/US2009/066992, dated Mar. 4, 2010, 15 pages.
International Search Report and Written Opinion for PCT/US2009/067992, Jul. 9, 2010, 20 pages.
International Search Report and Written Opinion for PCT/US2009/067994, dated Jun. 10, 2010, 18 pages.
International Search Report and Written Opinion for PCT/US2010/036188, dated Sep. 14, 2010, 18 pages.
Restriction Requirement for U.S. Appl. No. 12/428,226, dated Apr. 27, 2011, 7 pages.
Response to Restriction Requirement for U.S. Appl. No. 12/428,226, dated May 27, 2011, 10 pages.

Office Action for U.S. Appl. No. 12/428,226, dated Jun. 9, 2011, 8 pages.
Office Action for U.S. Appl. No. 12/543,000, dated Mar. 15, 2011, 14 pages.
Fritscher-Ravens, "Transgastric endoscopy—a new fashion, a new excitement!", *Endoscopy*, vol. 39, 2007, pp. 161-167.
Sporn et al., "Endoscopic colotomy closure after full thickness excision: comparison of T fastener with mutliclip applier", *Endoscopy*, vol. 40, 2008, pp. 589-594.
Voermans et al., "In vitro comparison and evaluation of seven gastric closure modalities for natural orifice transluminal endoscopic surgery", *Endoscopy*, vol. 40, 2008, pp. 595-601.
Sclabas et al., "Endoluminal Methods for Gastrotomy Closure in Natural Orifice TransEnteric Surgery", *Surgical Innovation*, vol. 13, No. 1, Mar. 2006, pp. 23-30.
Desilets et al., "Loop-anchor purse-string versus endoscopic clips for gastric closure: a natural orifice transluminal endoscopic surgery comparison study using burst pressures", *Gastrointestinal Endoscopy*, vol. 70, No. 6, 2009, pp. 1225-1230.
Sporn et al., "Endoscopic colotomy closure for natural orifice transluminal endoscopic surgery using a T-fastener protoype in comparison to conventional laparoscopic suture closure", *Gastrointestinal Endoscopy*, vol. 68, No. 4, 2008, pp. 724-730.
Dray et al., "Air and fluid leak tests after NOTES procedures: a pilot study in a live porcine model", *Gastrointestinal Endoscopy*, vol. 68, No. 3, 2008, pp. 513-519.
Shurr et al., "An over-the-scope clip (OTSC) system for closure of iatrogenic colon perforations: results of an experimental survival study in pigs", *Endoscopy*, vol. 40, 2008, pp. 584-588.
Romanelli et al, "Natural orifice transluminal endoscopic surgery gastrotomy closure in porcine explants with the Padlock-G clip using the Lock-It system", *Endoscopy*, vol. 42, 2010, pp. 306-310.
Bergström et al., "Early clinical experience with a new flexible endoscopic suturing method for natural orifice transluminal endoscopic surgery and intraluminal endosurgery", *Gastrointestinal Endoscopy*, vol. 67, No. 3, 2008, pp. 528-533.
Park et al, "Endoscopic sutured closure of a gastric natural orifice transluminal endoscopic surgery access gastronomy compared with open surgical closure in a porcine model. A randomized, multicenter controlled trial", *Endoscopy*, vol. 42, 2010 pp. 311-317.
Yasser M. Bhat, MD, "Transluminal Endosurgery: Novel Use of Endoscopic Tacks for the Closure of Access Sites in Natural Orifice Transluminal Endoscopic Surgery," *Gastrointestinal Endoscopy*, vol. 69, No. 6, p. 1161.

* cited by examiner

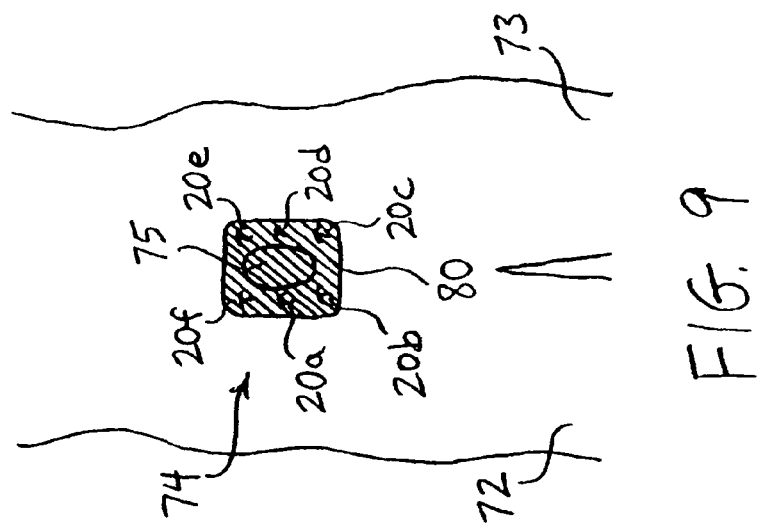
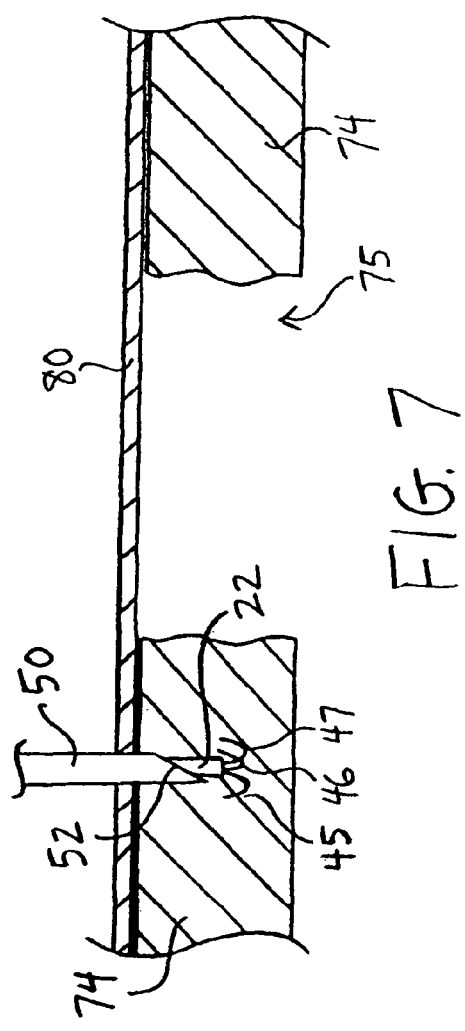
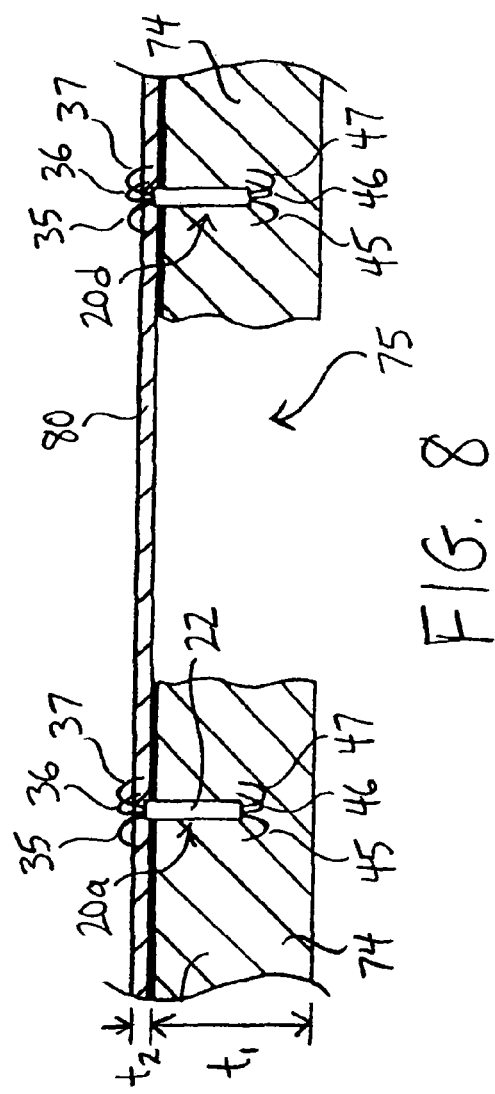

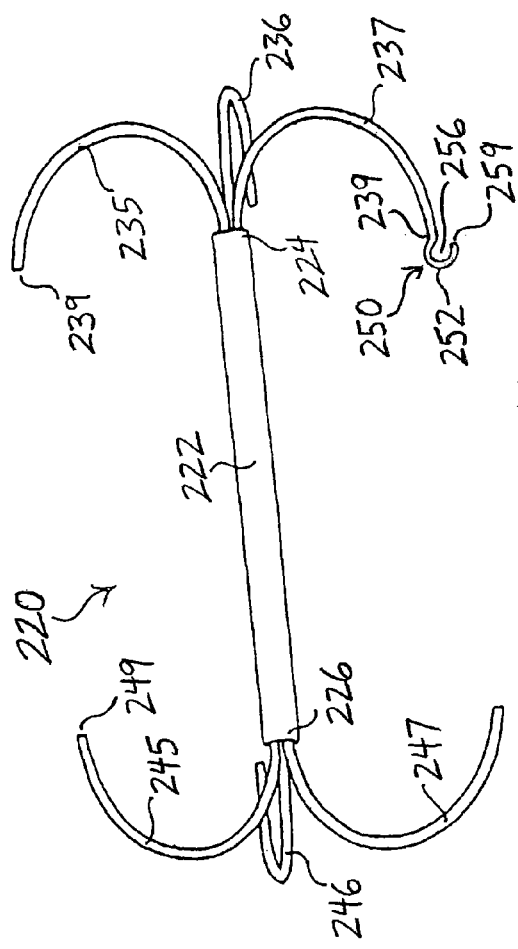
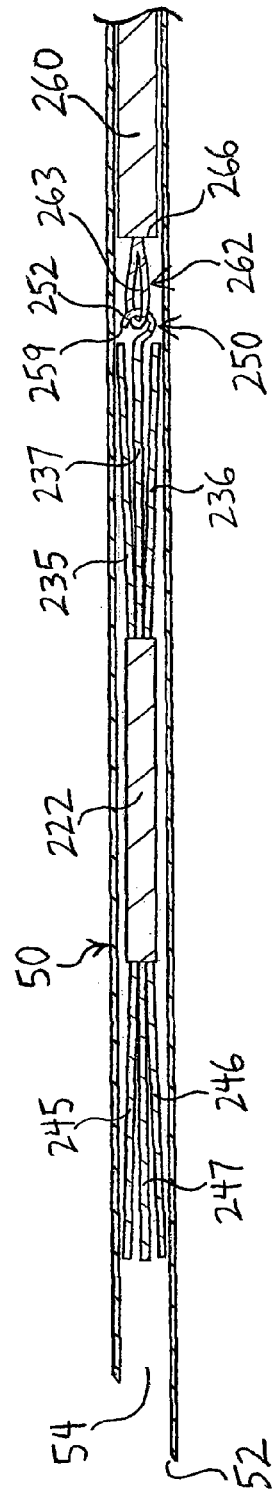

RETRACTABLE TACKING DEVICE

PRIORITY CLAIM

This invention claims the benefit of priority of U.S. Provisional Application Ser. No. 61/121,067, entitled "Retractable Tacking Device," filed Dec. 9, 2008, the disclosure of which is hereby incorporated by reference in its entirety.

BACKGROUND

The present embodiments relate generally to medical devices, and more particularly, to apparatus and methods for coupling a graft member to tissue or closing a bodily opening.

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons.

Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of a ventral abdominal hernia, the sutures may be threaded through the thickness of the abdominal wall, then tied down and knotted. However, such manual suturing techniques may be time consuming and/or difficult to perform.

Further attempts to seal intentional or unintentional openings in tissue have been performed using mechanical devices such as clips, tacks, staples, and fasteners. Such devices may be delivered towards a target tissue site and deployed to engage tissue surrounding the opening. However, typically once such mechanical devices are deployed, they are permanently engaged to the tissue and cannot be recaptured or repositioned, resulting in possible permanent deployment of such devices at an undesirable location.

SUMMARY

The present embodiments provide a tacking device for engaging tissue, which may be useful for coupling a graft to tissue or facilitating closure of a bodily opening. In one embodiment, the tacking device comprises a main body having proximal and distal ends, and further comprises at least one proximal deployable member and at least one distal deployable member, each having contracted and expanded states. The proximal deployable members extend proximally from the proximal end of the main body, while the distal deployable members extend distally from the distal end of the main body. A hook member extends from at least one of the proximal deployable members. In use, the hook member may be engaged, for example, using a loop member coupled to a stylet, to facilitate controlled release of the tacking device and allow repositioning of the tacking device after at least partial deployment of the distal deployable members.

In one embodiment, the hook member may comprise a substantially identical configuration when the proximal and distal deployable members are in the expanded and contracted states. The proximal and distal deployable members each may comprise hook-shaped configurations in the expanded states that are substantially concave relative to the main body, while the hook member may comprise a substantially convex curvature relative to the main body when the proximal and distal deployable members are in the expanded states. Further, the proximal and distal deployable members each may comprise a substantially flat configuration in the contracted states, in which the hook member extends proximal to the proximal deployable members for engagement with the loop member.

An insertion tool comprising a hollow lumen may be used to deliver the tacking device. The tacking device may be disposed within the hollow lumen during delivery with the proximal and distal deployable members in the contracted states. The stylet is disposed for longitudinal movement within the hollow lumen of the insertion tool and is positioned proximal to the tacking device during delivery. The loop member extends from the distal end of the stylet and may be configured to be coupled to the hook member when the proximal deployable members are in the contracted states. The loop member further is configured to be disengaged from the hook member when the proximal deployable members are in the expanded states.

Advantageously, a tacking device provided in accordance with the present embodiments is recapturable after at least partial deployment of the distal deployable members. For example, after the distal deployable members have been at least partially expanded at the preliminary location, proximal retraction of the stylet is operative to effect proximal retraction of the distal deployable members, via the hook member coupled to the loop member, to thereby enable contraction of the distal deployable members into the hollow lumen of the insertion tool and permit repositioning at a final location. Alternatively, distal advancement of the insertion tool, relative to the stylet and tacking device, may be used to contract the distal deployable members within the hollow lumen of the insertion tool and permit repositioning at a final location. A physician therefore may reposition the tacking device if a preliminary deployment location or orientation within the tissue is undesirable, so long as the hook member and the loop member remain coupled together within the insertion tool.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 7 is a side-sectional view taken along line A—A of FIG. 6.

FIG. 8 is a side-sectional view showing multiple tacking devices deployed in expanded configurations.

FIG. 9 is a schematic view illustrating multiple deployed tacking devices used to treat the ventral hernia of FIG. 4.

FIG. 12 is a perspective view of a further alternative tacking device.

FIG. 13 is a side-sectional view of a distal region of an insertion tool and the tacking device of FIG. 12.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
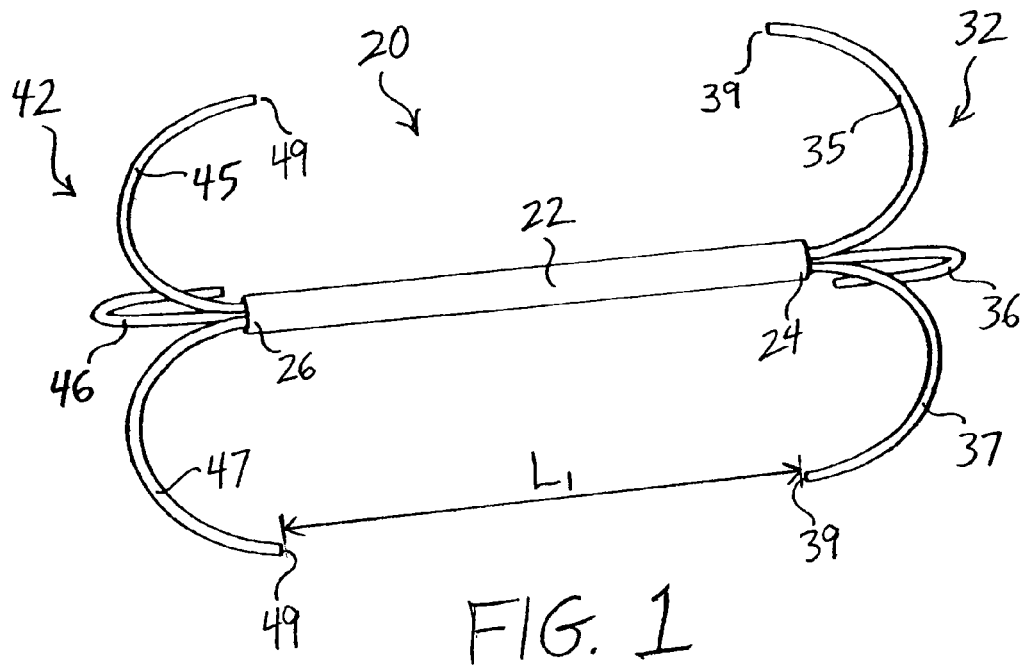
FIG. 1 is a perspective view of a tacking device.

Referring now to FIG. 1, a first embodiment of a tacking device 20 is shown. In this embodiment, the tacking device 20 comprises at least one tube member 22 having a proximal end 24 and a distal end 26. The tacking device 20 further comprises a proximal deployment mechanism 32 and a distal deployment mechanism 42. In the embodiment of FIG. 1, the proximal deployment mechanism 32 comprises three proximal deployable members 35-37, while the distal deployment mechanism 42 comprises three distal deployable members 45-47. The proximal deployable members 35-37 extend proximally from the proximal end 24 of the tube member 22, while the distal deployable members 45-47 extend distally from the distal end 26 of the tube member 22, as shown in FIG. 1. In the embodiment of FIG. 1, since the device is symmetrical, it may be loaded into an insertion tool with either end first, as explained further below.

The proximal deployable members 35-37 and the distal deployable members 45-47 each may be affixed relative to the tube member 22. In one embodiment, each of the proximal and distal deployable members 35-37 and 45-47 may be separate and discrete elements. Accordingly, six separate deployable members may be provided. Specifically, the three proximal deployable members 35-37 may be coupled to the tube member 22 near the proximal end 24 of the tube member 22. The three proximal deployable members 35-37 may be coupled to the proximal end 24 of the tube member 22 using an adhesive, frictional fit, mechanical device or other suitable mechanism or processes. Similarly, the three distal deployable members 45-47 may be coupled to the distal end 26 of the tube member 22 using an adhesive, frictional fit, mechanical device or other suitable mechanism.

In an alternative embodiment, instead of providing six discrete deployable members, three wires may be disposed through the entirety of tube member 22. In this embodiment, a first wire may comprise a proximal end that forms the deployable member 35 and a distal end that forms the deployable member 45, while a central region of the same wire is disposed through the entirety of the tube member 22. Similarly, second and third wires may be disposed through the entirety of the tube member 22 to form the remaining proximal and distal deployable members. In this embodiment, the three wires that extend through the length of the tube member 22 may be affixed to an interior surface of the tube member 22, for example, using an adhesive or mechanical device. The three wires also may be sized to create a frictional fit against each other and/or an interior surface of the tube member 22, thereby inhibiting movement of the proximal and distal deployable members 35-37 and 45-47 in longitudinal directions with respect to the tube member 22.

While six total deployable members 35-37 and 45-47 are depicted, including three at both the proximal and distal ends of the tacking device 20, it will be apparent that greater or fewer deployable members may be employed. Moreover, the deployable members 35-37 and 45-47 may comprise any shape suitable for engaging, penetrating and/or abutting tissue, for purposes explained further below, and need not necessarily assume the expanded shape depicted in FIGS. 1-2.

The tube member 22 may comprise any suitable shape and material. Solely by way of example, the tube member 22 may comprise stainless steel or a biocompatible plastic. The tube member 22 may be cylindrically-shaped, as depicted in FIG. 1, which may facilitate insertion through a lumen of an insertion tool 50. Further, the tube member 22 may comprise one solid tube, or alternatively may comprise one or more tubes that may comprise slots, holes, cut-out regions and the like, for example, as shown and explained below with respect to the embodiment of FIGS. 10-11.

Alternatively, as explained further below with respect to FIG. 10, the tube member 22 may be omitted entirely in the case where a first wire 125 integrally forms the proximal and distal deployable members 135 and 145, a second wire 126 integrally forms the proximal and distal deployable members 136 and 146, and a third wire 127 integrally forms the proximal and distal deployable members 137 and 147. In the latter embodiment, central regions of the first, second and third wires 125-127 may be affixed together, for example, using a solder or weld, to maintain the structural rigidity of the components.

Figure 2:
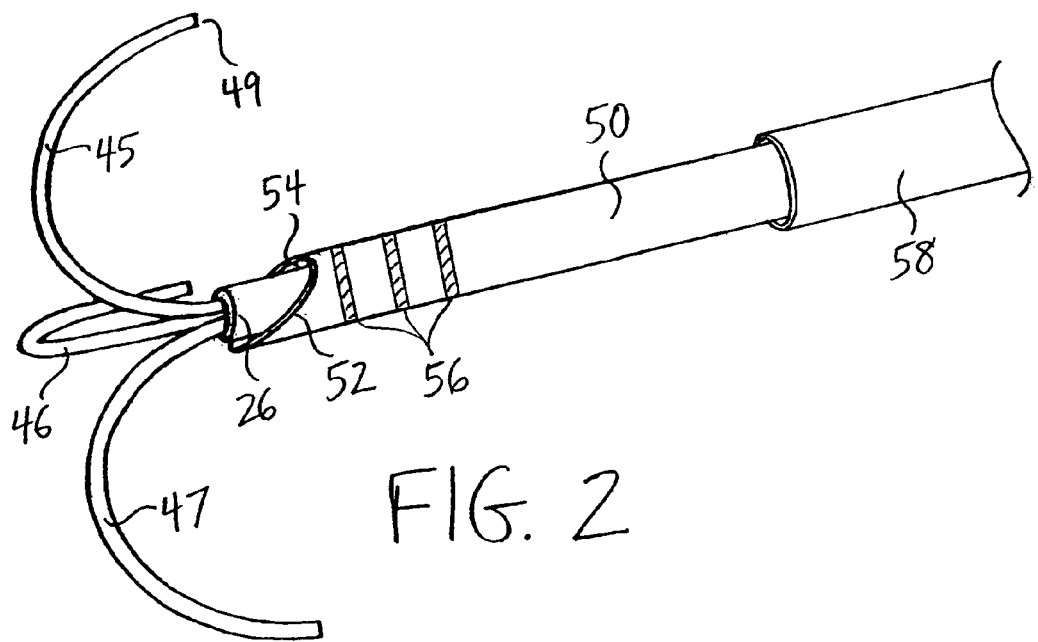
FIG. 2 is a perspective view of a distal region of an insertion tool and the tacking device of FIG. 1.
Figure 3:
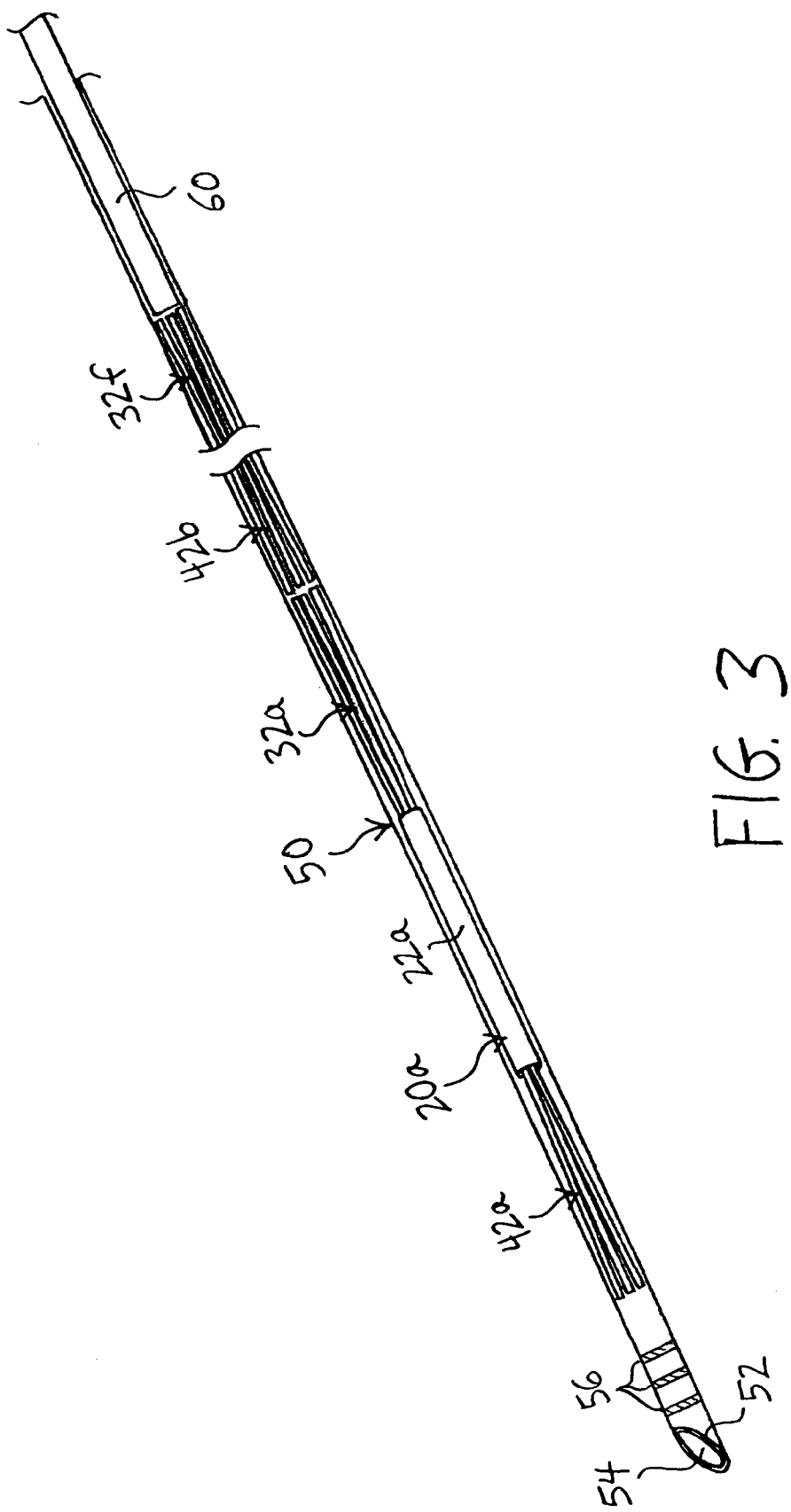
FIG. 3 is a perspective, cut-away view illustrating multiple tacking devices in a delivery configuration.

Referring still to FIGS. 1-3, the proximal and distal deployable members 35-37 and 45-47 each comprise a contracted delivery configuration, as shown in FIG. 3 below, and further comprise an expanded deployed configuration, as shown in FIG. 1. In one embodiment, each of the deployable members 35-37 and 45-47 may comprise a hook-shaped configuration in the expanded state. For example, the deployable members 35-37 and 45-47 may comprise a curvature of about 90 to about 360 degrees in the expanded state, and more preferably about 180 degrees, as shown in FIGS. 1-2. Where the deployable members 35-37 and 45-47 "retroflex" and comprises a curvature of about 180 degrees, the end regions 39 and 49 of the proximal and distal deployable members are oriented substantially parallel to the tube member 22. Moreover, the end regions 39 and 49 may be radially spaced apart from one another in the expanded state, as shown in FIG. 1. In this configuration, the end regions 39 and 49 may be well-suited for engaging, grasping, piercing and/or abutting tissue or graft material.

Further, a longitudinal distance $L_1$ between the end regions 39 and 49 of the tacking device 20 may be varied to engage tissue in a desirable manner. For example, the longitudinal distance $L_1$ may be dimensioned to be substantially equal to or less than the combined thickness $t_1$ and $t_2$ of a tissue 74 and a graft member 80, respectively, as shown in FIG. 8 below, thereby providing a desired compressive force upon the tissue 74 and the graft member 80.

The dimensions of the tacking device 20 may be tailored based on a particular surgical procedure, a particular patient's anatomy and/or other factors. However, for illustrative purposes, in a ventral hernia repair operation, the longitudinal length of the tube member 22 may range from about 2 mm to about 10 mm, the straightened (delivery or non-curved) length of the proximal deployable members 35-37 may range from about 5 mm to about 50 mm, the straightened (delivery or non-curved) length of the distal deployable members 45-47 may range from about 5 mm to about 50 mm, the longitudinal distance $L_1$ between the end regions 39 and 49 may range from about 5 mm to about 30 mm, the outer diameter of the tube member 22 may range from about 0.3 mm to about 1.5 mm, and the outer diameter of the deployable member 35-37 and 45-47 may range from about 0.1 mm to about 0.5 mm. Such dimensions are provided for reference purposes only and are not intended to be limiting.

The deployable members 35-37 and 45-47 may comprise a shape-memory material, such as a nickel-titanium alloy (nitinol). If a shape-memory material such as nitinol is employed, the deployable members 35-37 and 45-47 may be manufactured such that they can assume the preconfigured expanded state shown in FIG. 1 upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial, predetermined configuration, as shown in FIG. 1. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the deployable members 35-37 and 45-47 may be made from other metals and alloys that are biased, such that they may be restrained by the insertion tool 50 prior to deployment, but are inclined to return to their relaxed, expanded configuration upon deployment. Solely by way of example, the deployable members 35-37 and 45-47 may comprise other materials such as stainless steel, cobalt-chrome alloys, amorphous metals, tantalum, platinum, gold and titanium. The deployable members 35-37 and 45-47 also may be made from non-metallic materials, such as thermoplastics and other polymers. As noted above, the deployable members 35-37 and 45-47 may comprise any shape suitable for engaging, penetrating and/or abutting tissue, for purposes explained further below, and need not necessarily assume the curved shape depicted in FIGS. 1-2.

Referring to FIGS. 2-3, one or more tacking devices 20 may be delivered to a target site in a patient's anatomy using an insertion tool 50. In one embodiment, the insertion tool 50 is capable of carrying multiple different tacking devices, such as six tacking devices 20a-20f, as shown in FIG. 9 and described below. In FIG. 3, one complete tacking device 20a is shown in the contracted state, while portions of the proximal deployment mechanism 42b of another tacking device 20b, and the distal deployment mechanism 32f of another tacking device 20f, are also shown.

In one embodiment, the insertion tool 50 comprises a needle-like body having a sharpened distal tip 52 and a hollow lumen 54, as shown in FIGS. 2-3. The insertion tool 50 may be manufactured from stainless steel or any other suitable material, and may comprise an endoscopic ultrasound (EUS), or echogenic, needle. Solely by way of example, the insertion tool 50 may comprise the EchoTip® Ultrasound Needle, or the EchoTip® Ultra Endoscopic Ultrasound Needle, both manufactured by Cook Endoscopy of Winston-Salem, N.C.

The hollow lumen 54 of the insertion tool 50 may comprise an inner diameter than is larger than an outer diameter of the tacking device 20. Therefore, one or more tacking devices, such as six tacking devices 20a-20f, may be loaded into the hollow lumen 54 in a delivery configuration, as shown in FIG. 3. In the delivery configuration, the proximal and distal deployable members 35-37 and 45-47 of each tacking device 20a-20f may comprise a substantially longitudinally-oriented profile, i.e., oriented along a longitudinal axis of the insertion tool 50.

The multiple tacking devices 20a-20f may be inserted into the hollow lumen 54 of the insertion tool 50 in a sequential manner, whereby the proximal deployment mechanism 32a of the first tacking device 20a may abut the distal deployment mechanism 42b of the second tacking device 20b, as depicted in FIG. 3. The distal deployment mechanism 42a of the first tacking device 20a may be loaded a distance away from the sharpened distal tip 52 of the insertion tool 50 to prevent inadvertent deployment.

A stylet 60 may be disposed for longitudinal movement within the hollow lumen 52 of the insertion tool 50, as shown in FIG. 3. The stylet 60 may comprise stainless steel or any other suitable material. The stylet 60 is disposed proximal to the proximal deployment mechanism 32f of the final sequential tacking device 20f, as shown in FIG. 3. During use, the insertion tool 50 may be proximally retracted, while the stylet 60 may be held longitudinally steady, to facilitate sequential deployment of each of the tacking devices 20a-20f, as explained further below.

The insertion tool 50 may comprise one or more markers 56, as shown in FIGS. 2-3, which may be disposed near the distal end of the insertion tool 50. The markers 56 may be configured to be visualized under fluoroscopy of other imaging techniques to facilitate location of the distal end of the insertion tool, for example, so that a physician may determine how far the insertion tool 50 has penetrated into tissue 74, as depicted in FIGS. 7-8. Optionally, a sheath member 58 having an inner diameter larger than an outer diameter of the insertion tool 50, as shown in FIG. 2, may be longitudinally advanced over the insertion tool 50, for various purposes explained further below. As will be explained further below, the insertion tool 50 may be used in conjunction with another device, such as an endoscope, and may be delivered through a working lumen of an endoscope or similar device.

Referring now to FIGS. 4-9, one or more tacking devices 20 described above may be used to facilitate treatment of a perforation 75 using a graft member 80. In the example shown, the perforation 75 is a ventral hernia located in the abdominal wall 74. The right and left legs 72 and 73 of a patient 70 are shown for illustrative purposes. While treatment of a ventral hernia is shown for illustrative purposes, it will be apparent that the tacking devices described herein may be used in a wide range of medical procedures, including but not limited to any exemplary procedures described herein.

Figures 4, 5:
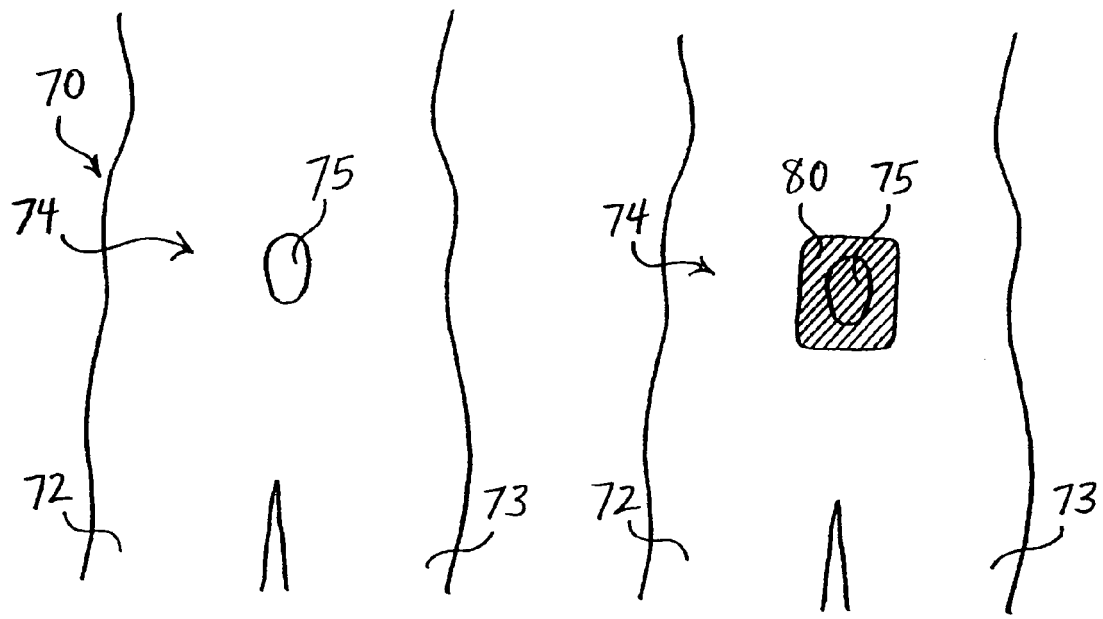
FIG. 4 is a schematic view illustrating a ventral hernia.
FIG. 5 is a schematic view illustrating a graft member used to cover the ventral hernia of FIG. 4.

The initial stages of the ventral hernia repair may be performed using techniques that are known. Specifically, an open technique or laparoscopic technique may be employed. In an open technique, an incision may be made in the abdominal wall and fat and scar tissue may be removed from the area. A graft member 80 then may be applied so that it overlaps the perforation 75, preferably by several millimeters or centimeters in each direction, as depicted in FIG. 5. In a laparoscopic technique, two or three smaller incisions may be made to access the hernia site. A laparoscope may be inserted into one incision, and surgical instruments may be inserted into the other incision(s) to remove tissue and place the graft member 80 in the same position as the open procedure.

The graft member 80 may comprise any suitable material for covering the perforation 75 and substantially or entirely inhibiting the protrusion of abdominal matter. In one embodiment, the graft member 80 may comprise small intestinal submucosa (SIS), such as SURGISIS® BIODESIGN™ Soft Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the graft member 80 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 80 may also comprise a composite of a biomaterial and a biodegradeable polymer. Additional details may be found in U.S. Pat. No. 6,206,931 to Cook et al., the disclosure of which is incorporated herein by reference in its entirety.

Figure 6:
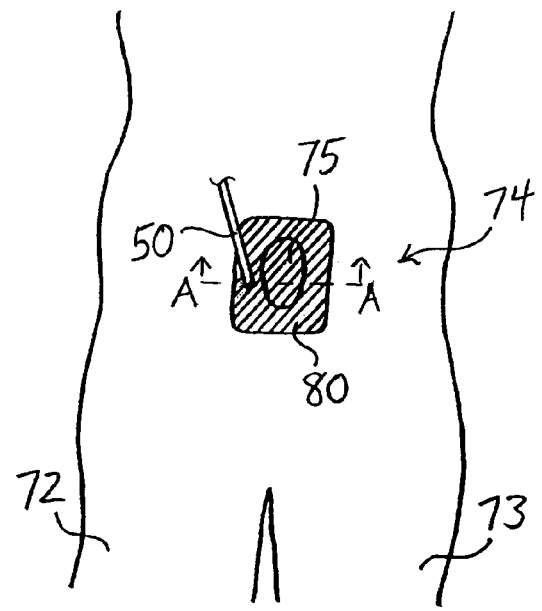
FIG. 6 is a schematic view of a method step for treating the ventral hernia of FIG. 4.

Referring now to FIGS. 6-7, after the graft member 80 has been placed to cover the perforation 75, the insertion tool 50 may be advanced in a distal direction to pierce through the graft member 80, and further may pierce at least partially into the tissue 74 at a first location around the perimeter of the perforation 75. In this example, the insertion tool 50 is carrying six sequential tacking devices 20a-20f, which may be disposed within the hollow lumen 54 of the insertion tool 50 as shown and explained with respect to FIG. 3 above. With each of the tacking devices 20a-20f in the contracted delivery states, the sharpened tip 52 of the insertion tool 50 may be advanced to a predetermined depth into the tissue 74. The markers 56 of FIGS. 2-3 may facilitate in determining how far the insertion tool 50 has penetrated into tissue 74, as depicted in FIG. 7.

In a next step, the stylet 60 of FIG. 3 may be held steady with respect to the insertion tool 50, while the insertion tool 50 is retracted in a proximal direction. This causes the distal deployable members 45-47 of the most distal tacking device 20a to extend distal to the sharpened tip 52 of the insertion tool 50, as depicted in FIG. 7. When the distal deployable members 45-47 are no longer radially constrained by the insertion tool 50, they may assume their predetermined expanded configurations in which they may engage, penetrate and/or abut the tissue 74. As the insertion tool 50 further is retracted proximally with respect to the tacking device 20a, the proximal deployable members 35-37 may assume their predetermined expanded configuration when are no longer radially constrained, as shown in FIG. 7. In the expanded configuration, the proximal deployable members 35-37 may engage, penetrate and/or abut the graft member 80 and optionally penetrate into the tissue 74. In this manner, the tacking device 20a helps secure the graft material 80 against the tissue 74. In particular, the substantially 180-degree hook-shaped configuration of the proximal deployable members 35-37 may urge the graft member 80 in a distal direction towards the tissue 74.

After the first tacking device 20a has been deployed, the insertion tool 50 may be repositioned to deploy another tacking device around the perimeter of the perforation 75. Each subsequent tacking device 20b-20f may be deployed in the same manner as the tacking device 20a. In this manner, the tacking devices 20a-20f may secure the graft member 80 around the perimeter of the perforation 75, as shown in FIG. 9. As will be apparent, greater or fewer tacking devices may be used, and the positioning of the tacking devices may be varied to optimize securing the graft member 80 to the tissue 74 in order to substantially seal the perforation 75.

Optionally, the sheath member 58 of FIG. 2 may be longitudinally advanced over the insertion tool 50, for example, if needed to protect the sharpened distal tip 52 of the insertion tool 50 while the insertion tool 50 is being repositioned. Further, the sheath member 58 may be advanced distally over the insertion tool 50 to facilitate deployment of the proximal deployable members 35-37. For example, the sheath member 58 may periodically push against the graft member 80, thereby temporarily urging the graft member 80 and/or the tissue 74 in a distal direction. At this time, the sheath member 58 may be held steady while the insertion tool 50 is retracted proximally to deploy the proximal deployable members 35-37 at a location proximal to the compressed tissue 74 and graft member 80. Once the proximal deployable members 35-37 have been deployed, the compressive force applied by the sheath member 58 may be removed so that the graft member 80 and the tissue 74 may engage the deployed proximal deployable members 35-37.

In the embodiment of FIGS. 4-9, the tissue 74 illustratively comprises a thickness $t_1$, while the graft member 80 comprises a thickness $t_2$. The distal deployable members 45-47 may be deployed entirely within the tissue 74, as depicted in FIG. 8, or alternatively may be deployed substantially distal to the tissue 74 while abutting or piercing through a distal edge of the tissue 74. In the latter embodiment, the longitudinal distance $L_1$ between the end regions 39 and 49 of the tacking device 20 may be dimensioned to be substantially equal to, or slightly less than, the combined thickness $t_1+t_2$ of the tissue 74 and the graft member 80. The longitudinal distance $L_1$ may be otherwise sized and configured, as desired, to apply desired forces upon the graft member 80 and the tissue 74.

While FIGS. 4-9 have illustrated the use of one or more tacking device 20 for covering a perforation 75 formed in the ventral abdominal wall, the tacking devices disclosed herein may be useful in many other procedures. Solely by way of example, one or more tacking devices 20 may be used to treat perforations in a visceral wall, such as the stomach wall. In such cases, a suitable insertion device, such as an endoscope, may be advanced through a bodily lumen such as the alimentary canal to a position proximate the target location. One or more components may be advanced through a working lumen of the endoscope. To close the perforation, the graft member 80 may cover the perforation and may be secured in a position overlapping the perforation using the one or more of the tacking devices 20, which may be deployed using the techniques described hereinabove.

Figure 10:
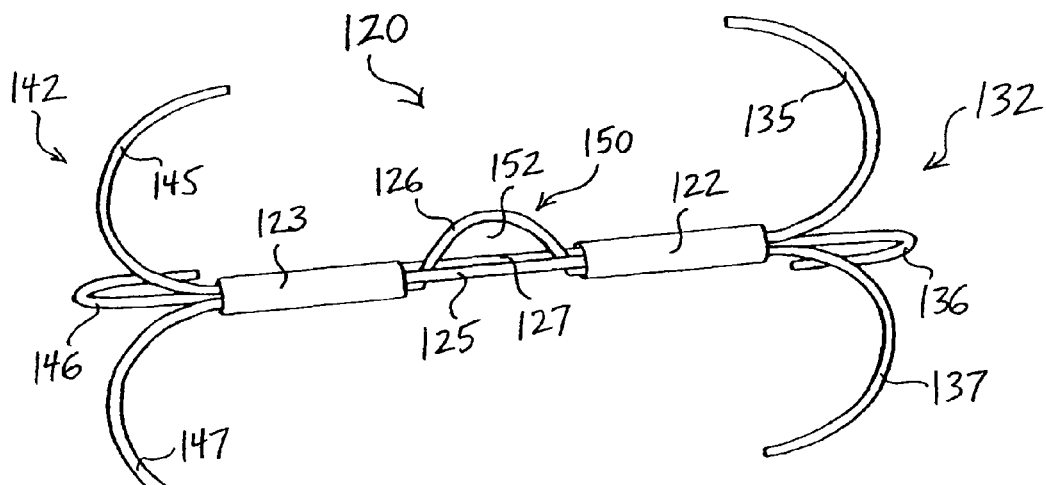
FIG. 10 is a perspective view of an alternative tacking device.

Referring now to FIG. 10, in an alternative embodiment, a tacking device 120 may comprise one or more features for facilitating suturing, and preferably purse-string suturing. The tacking device 120 is similar to the tacking device 20 of FIG. 1, except as noted below. The tacking device 120 comprises proximal and distal deployable members 135-137 and 145-147, respectively. In this embodiment, the tacking device 120 comprises a proximal tube portion 122 and distal tube portion 123 with an opening, slot or cutout disposed therebetween, as shown in FIG. 10. First, second and third wires 125-127 may be disposed through the entirety of the proximal and distal tube portions 122 and 123, as depicted in FIG. 10.

The first wire 125 may comprise a proximal end that forms deployable member 135 and a distal end that forms deployable member 145, such that a central region of the first wire 125 is disposed through both tube portions 122 and 123. Similarly, the second and third wires 126 and 127 may be disposed through the entirety of the tube portions 122 and 123. The second wire 126 may comprise a proximal end that forms deployable member 136 and a distal end that forms deployable member 146, while the third wire 127 may comprise a proximal end that forms deployable member 137 and a distal end that forms deployable member 147. The three wires 125-127 may be affixed to an interior surface of the tube portions 122 and 123, for example, using an adhesive, frictional fit or mechanical device. Alternatively, the tube portions 122 and 123 may be omitted, and central regions of the first, second and third wires 125-127 may be affixed to one another, for example, using a solder or weld.

In the embodiment shown, the second wire 126 comprises a loop member 150, which may be formed by bending a central region of the wire that is disposed between the tube portions 122 and 123, as shown in FIG. 10. The second wire 126 may be bent to form an arch-shaped loop member 150 having an aperture 152. A suture 160 may be threaded through the aperture 152 of the loop member 150, for example, as shown in FIG. 11 below.

In alternative embodiments, one single tube member may be employed, in lieu of the proximal and distal tube portions 122 and 123, and the single tube member may comprise a slot or cutout, such that the loop member 150 may extend radially through the slot or cutout. There also may be a single strip of material connecting the proximal and distal tube portions 122 and 123. Further, the loop member 150 need not be formed integrally from any of the wires 125-127, but rather may be formed as a loop disposed on an exterior surface of the proximal and distal tube portions 122 and 123, or on an exterior surface of a single tube member if only one tube is used. Still further, while the loop member 150 is shown in a substantially central location, it may be placed closer to the proximal or distal ends of the tacking device 120.

Figure 11:
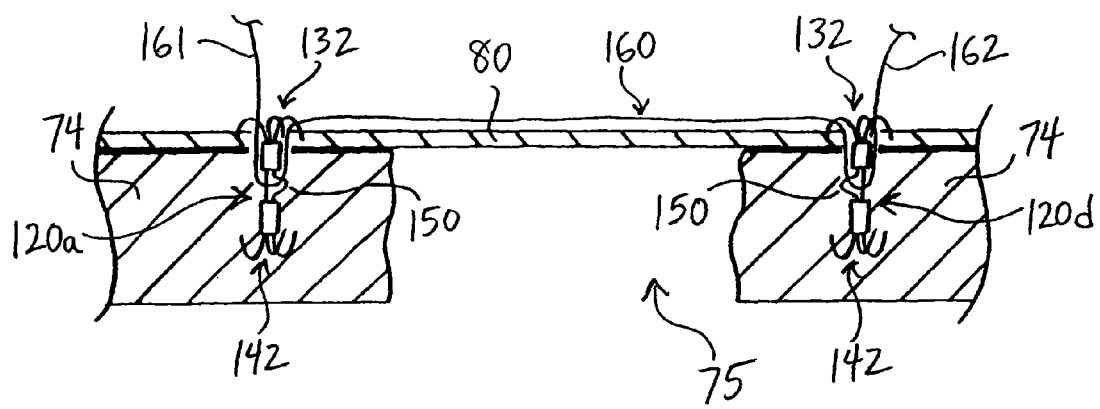
FIG. 11 is a side-sectional view illustrating one method of use of multiple tacking devices of FIG. 10.

Referring now to FIG. 11, an exemplary method of using the tacking device 120 is shown. In one step, a graft member 80 may be placed over a perforation 75, and multiple tacking devices 120 may be deployed using an insertion device to secure the graft member 80 to the tissue 74, as explained in detail above with respect to FIGS. 4-9. In the embodiment of FIG. 11, multiple tacking devices 120 may be linked together by a single suture 160, which may be slidably coupled through the loop members 150 of each of the tacking devices 120, as generally shown in FIG. 11. There are two free ends 161 and 162 of the suture 160, which may be independently tensioned to facilitate closure of the perforation 75.

Preferably, multiple tacking devices 120 having loop members 150 are sequentially positioned around the perforation 75 in a semi-annular or annular shape, for example, as shown above in FIG. 9. The ends 161 and 162 of the suture 160 are then tensioned to reduce the distance between the tacking devices and compress the tissue 74 around the perforation 75. The suture ends 161 and 162 may be secured to maintain the compression of the tissue 74 using any suitable technique such as by forming a knot or using clamps, rivets and the like.

Further, in lieu of the loop members 150 described herein, other mechanisms for engaging and/or retaining sutures may be integrally formed with the tacking device 120 or externally attached thereto. Solely by way of example, such suture retaining mechanisms are explained in pending U.S. patent application Ser. No. 11/946,565, filed Nov. 28, 2007, the entire disclosure of which is hereby incorporated by reference in its entirety.

Various types of sutures 160 may be used in conjunction with embodiment of FIGS. 10-11. For example, synthetic sutures may be made from polypropylene, nylon, polyamide, polyethylene, and polyesters such as polyethylene terephthalate. These materials may be used as monofilament suture strands, or as multifilament strands in a braided, twisted or other multifilament construction.

Referring now to FIGS. 12-13, in an alternative embodiment, a tacking device 220 may comprise one or more features for facilitating "recapture" or repositioning after the tacking device has been at least partially deployed. The tacking device 220 is similar to the tacking device 20 of FIG. 1, with the main exceptions noted below. The tacking device 220 comprises a main body 222 having a proximal end 224 and a distal end 226. Proximal deployable members 235-237 extend proximally from the proximal end 224 of the main body 222, while distal deployable members 245-247 extend distally from the distal end 226 of the main body 222. Each of the proximal and distal deployable members 235-237 and 245-247 comprise end regions 239 and 249, respectively.

In the embodiment of FIGS. 12-13, a hook member 250 extends from at least one of the proximal deployable members 235-237, and may be used to facilitate repositioning of the tacking device 220. In particular, after the distal deployable members 245-247 have been at least partially expanded at a preliminary location, the distal deployable members 245-247 may be contracted within an insertion tool to permit repositioning at a different, final location, as explained in further detail below.

In this embodiment, one hook member 250 extends from the end region 239 of the proximal deployable member 237. The hook member 250 may be integrally formed with the proximal deployable member 237, i.e., as an integral extension of the end region 239. Alternatively, the hook member 250 may be coupled to the end region 239 of the proximal deployable member 237, for example, using a solder or weld, after the proximal deployable members 235-237 have been heat-set to deploy to their predetermined expanded shapes. Preferably, the hook member 250 is not heat-treated, and therefore, maintains a substantially constant configuration regardless of whether the proximal and distal deployable members are in the expanded or contracted states shown in FIGS. 12-13, respectively.

In one embodiment, the hook member 250 comprises a substantially convex curvature relative to the main body 222 when the proximal deployable members 235-237 are in the expanded states. In an alternative embodiment, however, the hook member 250 may comprise a substantially concave curvature relative to the main body 222 when the proximal deployable members 235-237 are in the expanded states, i.e., both the hook members 250 and the proximal deployable members 235-237 may curve in the same direction.

The curved portion 252 may comprise a reduced radius of curvature relative to the proximal deployable members 235-237. In one embodiment, the radius of curvature of the curved portion 252 of the hook member 250 is about 2 to about 15 times less than the radius of curvature of the proximal deployable members 235-237, and therefore, the hook member 250 may comprise a significantly smaller profile.

The curved portion 252 of the hook member 250 extends through an arc spanning from the end region 239 to a tip 259, forming an aperture portion 256 therein. The arc of the curved portion 252 may range from about 60 to about 330 degrees, and more preferably, between 180 and 270 degrees, as depicted in FIGS. 12-13. The arc preferably spans more than 60 degrees so that a loop member 262 may remain coupled thereto when positioned within the insertion tool 50, as shown in FIG. 13 below. Further, the arc preferably spans less than 330 degrees so that the loop member 262 can disengage from the hook member 250 when released from the insertion tool 50, as explained further in FIG. 18 below. As used in the embodiments of FIGS. 12-13, the term "loop member 262" encompasses an enclosed loop spanning 360 degrees, as depicted herein, but also encompasses a partial looped shape, for example, a hook-shape spanning greater than 60 degrees but less than 360 degrees.

Referring to FIG. 13, the tacking device 220 may be delivered towards a target site in a contracted state using the insertion tool 50 described in FIGS. 2-3 above. In the contracted state, the proximal and distal deployable members 235-237 and 245-247 may comprise a substantially flat profile, i.e., oriented substantially along a longitudinal axis of the insertion tool 50. Preferably, when the tacking device 220 is in the contracted state, the hook member 250 extending from the proximal deployable member 237 may extend proximal to the end regions 239 of the other proximal deployable members 235 and 236, as shown in FIG. 13. When the proximal and distal deployable members are in the contracted states, the hook member 250 preferably retains its curvature of between about 60 and about 330 degrees, and more preferably, between 180 and 270 degrees, as shown in FIG. 13.

A stylet 260 suitable for deploying the tacking device 220 is similar to the stylet 60 described in FIG. 3 above, with a main exception that loop member 262 having an aperture 263 extends distally from the distal end 266 of the stylet 260, as shown in FIG. 13. In use, the loop member 262 may be coupled to the hook member 250 outside of the body. For example, in one technique, the stylet 260 may be positioned within the hollow lumen 54 such that the loop member 262 extends distal to the sharpened tip 52 of the insertion tool 50. The hook member 250 then is coupled to the loop member 262 by placing the tip 259 of the hook member 250 through the aperture 263 of the loop member 262. The proximal deployable members 235-237 are contracted and the stylet 260 then is proximally retracted, thereby pulling the tacking device 220 into the hollow lumen 54 of the insertion tool 50 in a distal to proximal direction. However, other suitable loading techniques may be used.

It should be noted that when the tacking device 220 is loaded into the insertion tool 50, the loop member 262 cannot disengage from the hook member 250, so long as the insertion tool 50 covers a junction between the loop member 262 and the hook member 250. Preferably, a distance between the curved portion 252 of the hook member 250 and an inner wall of the insertion tool 50 is less than a cross-sectional width of the loop member 262. Therefore, the hook member 250 cannot significantly move around when loaded into the insertion tool 50 and the loop member 262 cannot disengage from the hook member 250 when loaded within the insertion tool 50. At this time, proximal retraction of the stylet 260 will yield a corresponding proximal retraction of the tacking device 220, and by contrast, distal advancement of the stylet 260 will yield a corresponding distal advancement of the tacking device 220.

Figure 14:
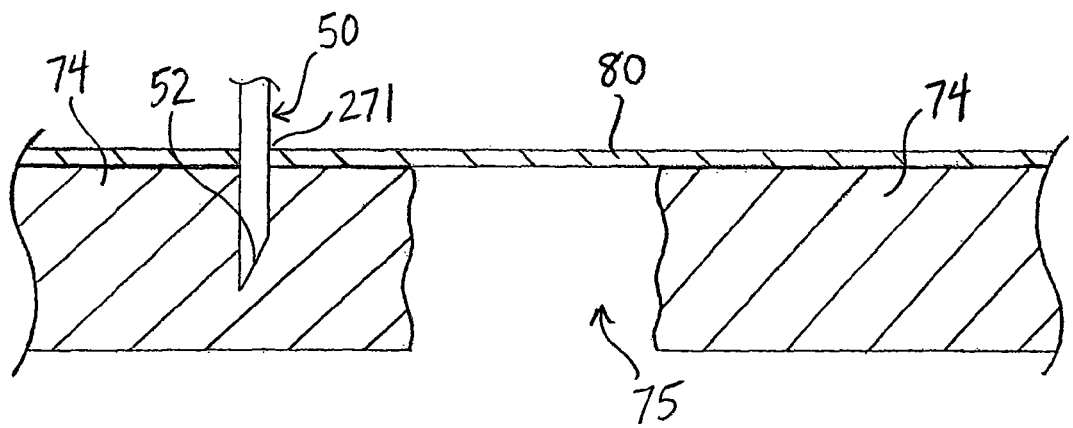
FIGS. 14-19 illustrate one exemplary method of use of the tacking device of FIGS. 12-13, with tissue shown from a side-sectional view, and device components shown from a side view for illustrative purposes.

Referring now to FIGS. 14-19, one exemplary method of use of the tacking device 220 is described to facilitate treatment of the ventral hernia perforation 75 previously described above. Using an open technique or laparoscopic technique, the graft member 80 may be applied so that it overlaps the perforation 75, preferably by several millimeters or centimeters in each direction, as depicted in FIG. 14. After the graft member 80 has been placed to cover the perforation 75, the insertion tool 50 may be advanced in a distal direction to pierce through the graft member 80 and at least partially into the tissue 74 at a preliminary location 271 near the perimeter of the perforation 75. At this time, the tacking device 220 is in the contracted delivery state shown in FIG. 13. The sharpened tip 52 of the insertion tool 50 may be advanced to a predetermined depth into the tissue 74, and the markers 56 of FIGS. 2-3 may facilitate in determining how far the insertion tool 50 has penetrated into tissue 74.

Figure 15:
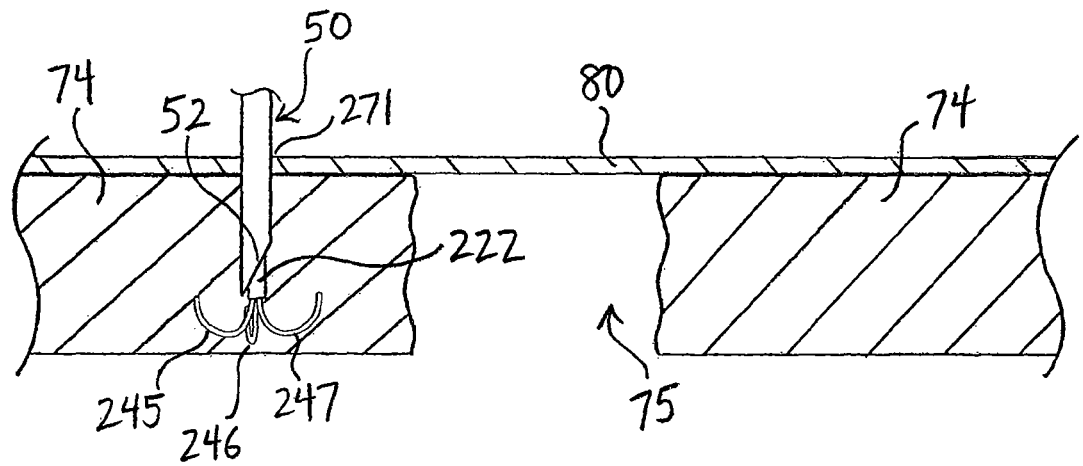

In a next step, the stylet 260 of FIG. 13 may be held steady with respect to the insertion tool 50, while the insertion tool 50 is retracted in a proximal direction with respect to the tacking device 220. Alternatively, the stylet 260 may be distally advanced, while the insertion tool 50 is held steady, to distally advance the tacking device 220 relative to the insertion tool 50. This causes the distal deployable members 245-247 of the tacking device 220 to extend distal to the sharpened tip 52 of the insertion tool 50, as depicted in FIG. 15. When the distal deployable members 245-247 are no longer radially constrained by the insertion tool 50, they may assume their predetermined expanded configurations in which they may engage, penetrate and/or abut the tissue 74.

In accordance with one aspect, the physician may determine that the tacking device 220 is not being deployed at a desired location. For example, the physician may realize that the main body 222 and/or the distal deployable members 245-247 have been deployed too close, or too far, from the perforation 75 in the tissue 74, or that the distal deployable members 245-247 have been deployed in an undesirable orientation. Since the loop member 262 is still engaged with the hook member 250 within the insertion tool 50, as described in FIG. 13, the physician may "recapture" and subsequently reposition the tacking device 220. In particular, in one technique, the physician may distally advance the insertion tool 50 while holding the stylet 260 steady, thereby distally advancing the insertion tool 50 relative to the tacking device 220 and over the distal deployable members 245-247, causing the distal deployable members 245-247 to assume the contracted state within the hollow lumen 54. In an alternative technique, the physician may proximally retract the stylet 260 while holding the insertion tool 50 steady, which retracts the tacking device 220 back into the hollow lumen 54 of the insertion tool 50 and into the contracted state, shown in FIG. 13. Preferably, the physician recaptures the distal deployable members 245-247 in the same manner in which they were deployed, i.e., either the insertion tool 50 is advanced and retracted while the stylet is always held steady, or vice versa.

Figure 16:
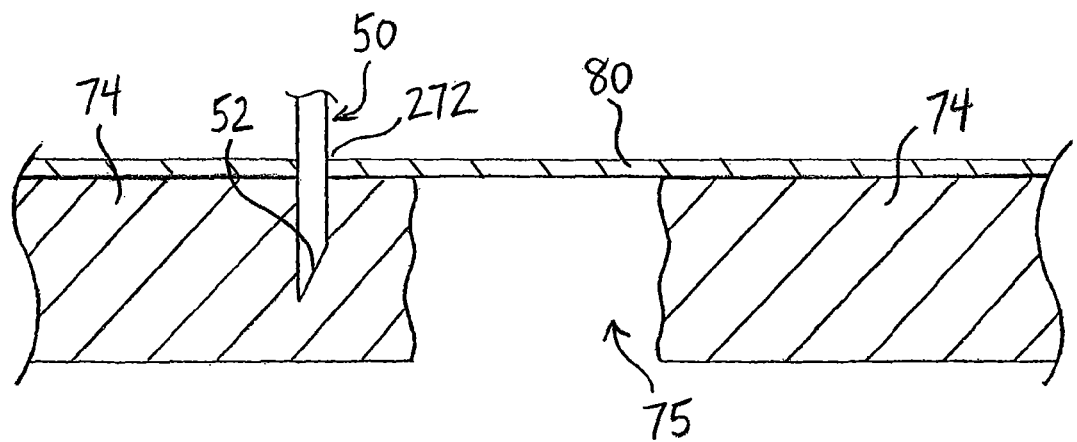
Figure 17:
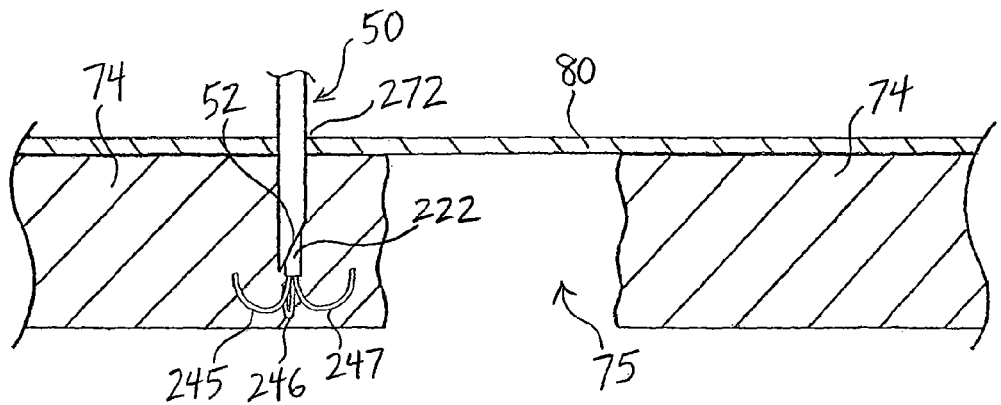

Referring now to FIGS. 16-17, in a next step, the physician may reposition the insertion tool 50 at another location within the tissue 74, such as a first final location 272. Optionally, the sheath member 58 of FIG. 2 may be longitudinally advanced over the insertion tool 50, for example, if needed to protect the sharpened distal tip 52 of the insertion tool 50 while the insertion tool 50 is being repositioned. The insertion tool 50 may pierce the tissue 74 at the first final location 272, as shown in FIG. 16, and the tacking device 220 may be distally advanced with respect to the insertion tool 50 to cause the distal deployable members 245-247 to engage the tissue 74, as shown in FIG. 17 and described above.

Figure 18:
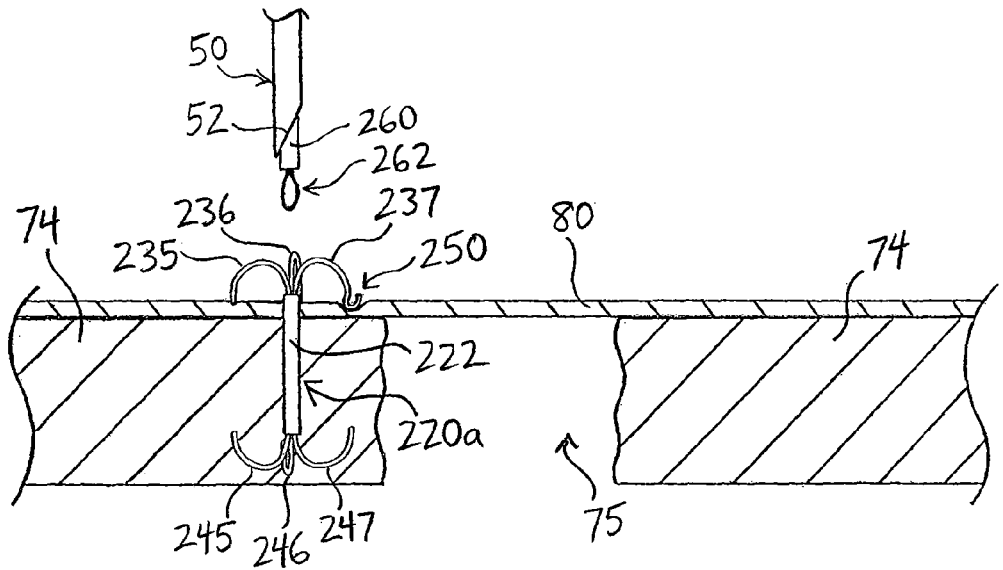

Referring now to FIG. 18, if the positioning of a first tacking device 220a is deemed acceptable, the physician then may release the first tacking device 220a. Specifically, the insertion tool 50 may be retracted proximally with respect to the first tacking device 220a, while the stylet 260 is held steady, to expose the junction between the hook member 250 and the loop member 262. When the insertion tool 50 passes the hook member 250 and the loop member 262, they can detach and release from each other. They may detach automatically once the insertion tool 50 no longer covers the junction, or if the loop member 262 remains disposed over the proximal deployable member 237 or hook portion 250, a physician may manipulate the stylet 260 as needed to disengage the loop member 262. The first tacking device 220a is left inside the body, with the distal deployable members 245-247 engaging the tissue 74 in the expanded state, and the proximal deployable members 235-237 engaging the graft member 80 in the expanded state to securely couple the graft member 80 to the tissue 74.

In a next step, the insertion tool 50 may be proximally retracted until the distal tip 52 is outside of the insertion device and the patient's body. A second tacking device 220b then may be loaded into the insertion tool 80, preferably in the same manner described above. In particular, the hook member 250 of the second tacking device 220b may be coupled to the loop member 262 of the stylet 260. Then the second tacking device 220b is loaded into the insertion tool 50 in a distal to proximal direction and assumes the contracted state shown in FIG. 13. The second tacking device 220b may be deployed at a final location in the tissue 74 in the manner described above for the first tacking device 220a. In this manner, any number of subsequent tacking device 220 may be inserted and deployed to at least partially surround the perimeter of the perforation 75 to secure the graft member 80 to the tissue 74.

In alternative embodiments, the hook member 250 may comprises other shapes than an arcuate shape. For example, curved portion 252 may be omitted, and the hook member 250 may comprise a shape having one or more right angles, such as a half-square or a three-quarter square shape, or any other shape suitable for engaging the loop member 262. Moreover, while one hook member 250 has been shown extending beyond the end region 239 of the proximal deployable member 237; such a hook member may be positioned at another location along any of the proximal deployable members 235-237, e.g., at a location closer to the main body 222.

Further, while the hook member 250 has been depicted on one single proximal deployable member 237, multiple hook members may be employed and may extend from each of the proximal deployable members 235-237.

Figure 19:
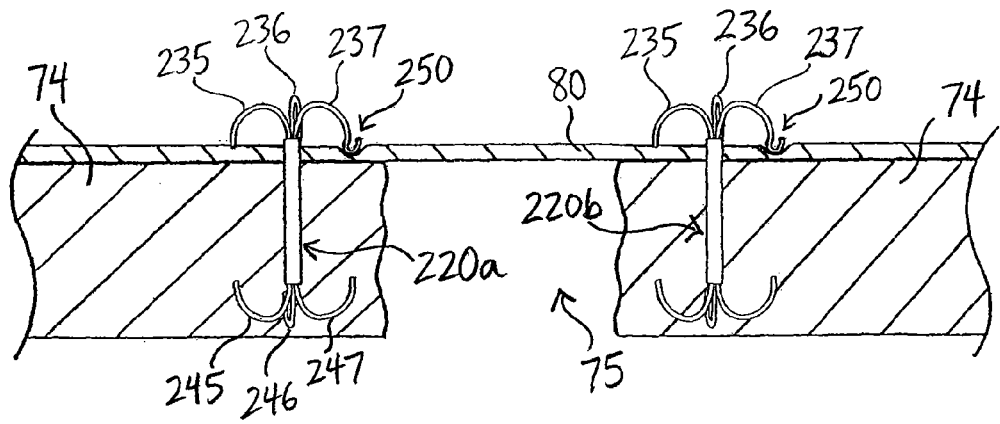

In a further alternative technique, after the proximal and distal deployable members 235-237 and 245-247 have been fully deployed, as shown in FIG. 19, a cinching member may be used to recapture one or more of the deployed tacking devices 220a and 220b. For example, the cinching member may comprise a loop portion having first and second elongated portions, wherein ends of the elongated portions may be actuated to adjust the size and configuration of the loop portion. The loop portion may be guided beneath at least one of the proximal deployable members 235-237 in an enlarged loop configuration, and then actuated to a smaller diameter by pulling on the first and second elongated portions. The loop portion then may be retracted proximally to collapse the proximal deployable members 235-237 into the contracted states shown in FIG. 13, at which time the hook member 250 may be re-engaged to the loop member 262 coupled to the stylet 260, and the stylet 260 may be retracted to retract the proximal deployable members 235-237 into the insertion tool. Then the distal deployable members 245-247 may be re-captured using the techniques described above to remove the previously fully deployed tacking devices.

While the examples shown above have illustratively described a tacking device that may be useful for coupling a graft member to tissue to cover and seal a perforation, the tacking devices 20, 120 and 220 also may be used in other procedures. As noted above, the tacking devices 20, 120 and 220 may be used to treat bodily walls during translumenal procedures. Further, the tacking devices 20, 120 and 220 may be used to secure a graft member to tissue for reconstructing local tissue, and the like.

In yet further applications within the scope of the present embodiments, the tacking devices 20, 120 and 220 need not be used for coupling a graft member to tissue. For example, the tacking devices 20, 120 and 220 may be used in an anastomosis procedure. In order to create an anastomosis, for example, multiple tacking devices 20, 120 and 220 may be deployed in a circular manner to couple a proximal vessel, duct or organ to a distal vessel, duct or organ. In such cases, a suitable insertion device, such as an endoscope, may be advanced through a bodily lumen such as the alimentary canal to a position proximate the target location. One or more components, such as the insertion tool 50, may be advanced through a working lumen of the endoscope. The distal end of the insertion tool 50 may be viewed under fluoroscopy, or via optical elements of the endoscope, or by some other visualization technique. Under suitable visualization, multiple tacking devices then may be delivered at one time, for example, using the insertion tool 50. Then, a hole may be punched through the middle of the deployed tacking devices to create a flow path between the proximal and distal vessels/ducts/organs. It will be apparent that still further applications of the tacking devices 20, 120 and 220 are possible. Moreover, the insertion tool 50 may be used with or without an endoscope or similar device.

In further alternative embodiments, the apparatus and methods described herein may be used for engaging a layer of material, and are not restricted to methods for treatment of a human or animal body by surgery or therapy. For example, a tacking device may be inserted with the proximal and distal deployable members in the contracted states, and the distal deployable members may be at least partially expanded to engage a layer of material at a preliminary location. A hook member extending from at least one of the proximal deployable members then may be proximally retracted to thereby proximally retract and contract the distal deployable members. The tacking device may be repositioned at a first final location, and the distal deployable members may be deployed to engage the layer of material in the expanded states at the first final location, as generally explained above.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A tacking device for engaging tissue, the tacking device comprising:
   a main body having proximal and distal ends;
   a plurality of proximal deployable members having contracted states during delivery and expanded states, wherein the proximal deployable members extend proximally from the proximal end of the main body;
   a plurality of distal deployable members having contracted states during delivery and expanded states, wherein the distal deployable members extend distally from the distal end of the main body and are configured to engage tissue in the expanded states; and
   a hook member extending from at least one of the proximal deployable members,
   wherein the hook member comprises a substantially identical configuration when the proximal and distal deployable members are in the expanded and contracted states,
   wherein the proximal deployable members and the distal deployable members each comprise hook-shaped configurations in the expanded states that are substantially concave relative to the main body,
   wherein a radius of curvature of the hook member is less than a radius of curvature of each of the proximal deployable members when the proximal and distal deployable members are in the expanded states, and wherein the hook member comprises a convex curvature relative to the main body when the proximal deployable members are in the expanded states.

2. The tacking device of claim 1 wherein the proximal and distal deployable members each comprise a substantially flat configuration in the contracted states, wherein the hook member extends proximal to the proximal deployable members when the proximal and distal deployable members are in the contracted states.

3. The tacking device of claim 1 further comprising:
   an insertion tool configured for delivery of the tacking device, the insertion tool comprising a hollow lumen, wherein the tacking device is disposed within the hollow lumen during delivery with the proximal deployable members and the distal deployable members in the contracted states;
   a stylet having proximal and distal ends and disposed for longitudinal movement within the hollow lumen of the insertion tool, wherein the stylet is positioned proximal to the tacking device during delivery of the tacking device; and
   a loop member extending from the distal end of the stylet, wherein the loop member is configured to be coupled to the hook member when the proximal deployable members are in the contracted states, and further is configured to be disengaged from the hook member when the proximal deployable members are in the expanded states.

4. The tacking device of claim 1 wherein a curved portion of the hook member extends from an end region of at least one of the proximal deployable members and terminates in a tip, wherein the curved portion spans between about 180 degrees to about 270 degrees between the end region and the tip.

5. The tacking device of claim 1 wherein the proximal deployable members and the distal deployable members comprise a nickel-titanium alloy that is configured to self-expand to the hook-shaped concave configurations in the expanded states.

* * * * *